US012285354B2

(12) United States Patent　(10) Patent No.: US 12,285,354 B2
Abramson et al.　(45) Date of Patent: Apr. 29, 2025

(54) FERTILITY-ENHANCING COOLING SEAT

(71) Applicants: David L. Abramson, Englewood, NJ (US); Steven A. Pentelnik, Cincinnati, OH (US); Wendy L. Everett, Red Wing, MN (US)

(72) Inventors: David L. Abramson, Englewood, NJ (US); Steven A. Pentelnik, Cincinnati, OH (US); Wendy L. Everett, Red Wing, MN (US)

( * ) Notice: Subject to any disclaimer, the term of this patent is extended or adjusted under 35 U.S.C. 154(b) by 1063 days.

(21) Appl. No.: 17/220,989

(22) Filed: Apr. 2, 2021

(65) Prior Publication Data

US 2021/0307959 A1　Oct. 7, 2021

Related U.S. Application Data

(60) Provisional application No. 63/004,235, filed on Apr. 2, 2020.

(51) Int. Cl.
*A61F 7/02*　(2006.01)
*A47C 7/74*　(2006.01)
*A61F 7/00*　(2006.01)

(52) U.S. Cl.
CPC .............. *A61F 7/02* (2013.01); *A47C 7/746* (2013.01); *A61F 2007/0048* (2013.01); *A61F 2007/0266* (2013.01); *A61F 2007/0269* (2013.01); *A61F 2007/0293* (2013.01)

(58) Field of Classification Search
CPC . A61G 5/1045; A61F 7/02; A61F 2007/0268; A47C 7/746
See application file for complete search history.

(56) References Cited

U.S. PATENT DOCUMENTS 6,132,455 A　10/2000　Shang
2014/0137316 A1　5/2014　Shoemake
(Continued)

FOREIGN PATENT DOCUMENTS

CN　201978011 U　9/2011

OTHER PUBLICATIONS

Chiba, Koji et al, "The Varicocele: Diagnostic Dilemmas, Therapeutic Challenges and Future Perspectives", Asian Journal of Andrology, (2016), 18, pp. 276-281.
Cho et al., "Effect of Varicocelectomy on Male Infertility", Korean J. Urol., Nov. 2014., 55(11):703-709.
(Continued)

*Primary Examiner* — Kaitlyn E Smith
(74) *Attorney, Agent, or Firm* — Christensen, Fonder, Dardi & Herbert PLLC

(57) ABSTRACT

A fertility-enhancing cooling seat for lowering temperatures of human testicles so as to increase sperm quality and quantity. The cooling seat includes: a top flexible portion and a base portion; a bottom flexible portion coupled to the top flexible portion, the bottom flexible portion forming a seal with the base portion, portions of the bottom flexible portion and portions of the top flexible portion defining isolated cooling cells with cooling-cell volumetric spaces; a phase-change material located in the cooling-cell volumetric spaces, the phase-change material configured to change from a solid phase to a liquid phase at a first temperature and that is configured to change from a liquid phase to a solid phase at a second temperature that is lower than the first temperature. At least one of the isolated cooling cells defines a diameter that is larger than a diameter of the other of the cooling cells.

19 Claims, 4 Drawing Sheets

(56) References Cited

U.S. PATENT DOCUMENTS

| | | |
|---|---|---|
| 2015/0025305 A1 | 1/2015 | Stringer et al. |
| 2015/0101786 A1 | 4/2015 | Xu |
| 2018/0021168 A1* | 1/2018 | Isaac .................. A61F 7/10 604/375 |
| 2019/0117447 A1* | 4/2019 | Doherty ............... A61F 7/02 |

OTHER PUBLICATIONS

Gulfam, R. et al., "Advanced Thermal Systems Driven by Paraffin-Based Phase Change Materials—A Review", Applied Energy, 2019, 238:582-611.

Hendershot, GE et al., "Infertility and age: an unresolved issue", Fam Plan Perspect., 1982 Sep.-Oct. 14(5):287-9, Abstract, 2 pages.

Hull, M G R et al., "Population Study of Causes, treatment, and outcome of infertility", British Medical Journal, vol. 291, pp. 1693-1697, Dec. 14, 1985.

Jung, A. at al., "Improvement of semen quality by nocturnal scrotal cooling in oligozoospermic men with a history of testicular maldescent", International Journal of Andrology, 2005, 28:93-98.

Mosher, W., "Infertility Trends Among U.S. Couples, 1965-1976", Family Planning Perspectives, 1982, vol. 14, 7 pages.

Peng, Benjamin C.H. et al., "The Cofactor Effect: Varicocele and Infertility", Fertility and Sterility, vol. 54, No. 1, Jul. 1990, pp. 143-148.

Walmart.com, Ergodrive Cooling Gel Enhanced Portable Non-Slip Seat Cushion, https://www.walmart.com/ip/Ergodrive-Cooling-Gel-Enhanced-Portable-Non-Slip-Seat-Cushion, Mar. 9, 2020, 7 pages.

Vakhshouri, A., "Paraffin as Phase Change Material", IntechOpen, Jan. 1, 2019, 23 pages.

* cited by examiner

FERTILITY-ENHANCING COOLING SEAT

PRIORITY CLAIM

This application claims the benefit of U.S. Provisional Patent Application No. 63/004,235, filed Apr. 2, 2020, which is incorporated herein in its entirety.

FIELD OF THE DISCLOSURE

The present disclosure relates to a fertility-enhancing cooling seat for human males. More specifically, the present disclosure relates to apparatuses, systems and methods relating to noninvasive cooling of human testicles to improve sperm quantity and quality.

BACKGROUND OF THE DISCLOSURE

Infertility is defined as not being able to get pregnant despite having unprotected sex for at least a year. In the United States, 15% of couples are infertile. One third of all infertility cases are solely attributed to the male partner, as described in: Mosher, W. 1982. "Infertility Among U.S. Couples, 1965-1976" Family Planning Perspectives. 14:22-27, which is herein incorporated by reference in its entirety.

Known causes of male infertility include abnormal sperm production or function, inability to deliver the sperm, or environmental factors. The most common cause of abnormal sperm quality is a varicocele, as described in: Nagler, H., et al. Varicocele: Lipshultz, Howard. Infertility in the Male, 3rd Ed. St. Louis, MO: Mosby-Year Book, 1997:336-359, which is herein incorporated by reference in its entirety. A varicocele is an enlargement of the veins within the scrotum, and it is believed that varicoceles increase the temperature of the testicles which causes abnormal sperm production. Further, it has been thought that tight clothes, or the use of hot baths and saunas may also be harmful to sperm production, as described in: Jung A. Schill W B, Schuppe H C: Improvement of semen quality by nocturnal scrotal cooling in oligozoospermic men with a history of testicular maldescent. Int J Androl. 2005, 28:93-98. 10.1111/j.1365-2605.2004.00517.x. which is incorporated by reference herein in its entirety. The ideal temperature for normal sperm production is 2-4° C. less than normal body temperature, as described in: Su et al. "Effect of Varicocelectomy on Male Infertility" Korean J Urol. 2014 Nov; 55 (11): 703-709, which is incorporated by reference herein in its entirety.

SUMMARY OF THE DISCLOSURE

Embodiments of the disclosure remedy the adverse effects of non-optimal temperature conditions, such as those caused by vericoceles, on sperm quantity and quality, by providing apparatuses, systems and methods directed to cooling the human scrotum, testicles and surrounding regions.

Further, embodiments of the disclosure include a number of advantageous features related to efficacy and convenience, as compared to other approaches to cooling human tissue. For example, a number of wearable or garment-like cooling devices for generally cooling portions of the male anatomy are known in the art. Publication Number US 2014/0137316 A1 to Shoemake, filed Nov. 21, 2012 and entitled "Men's Underwear with Fitted Frontal Pouch and Removable Ergonomic Gel Pack for Testicular Cooling," incorporated herein by reference it its entirety, describes a special undergarment configured to receive a gel pack that requires freezing. However, such a device is inconvenient to a user, and discourages regular, repeated use. A user must not only obtain and wear specialized undergarments with visibly bulky and potentially uncomfortable structure, but the insertable gel pack must be placed in a freezer to change back to a solid form prior to a second or subsequent use. Furthermore, the disclosed device fails to provide a consistent desired temperature profile over time due to the nature of the gel material used.

In addition to known such garment-based cooling devices, cooling pads for general use and comfort are known. For example, U.S. Pat. No. 6,132,455 to Shang, filed Feb. 5, 1999, and entitled "Cooling Comfort Seat Cushion" and Pub. No. US 2015/0101786 to Xu, filed Oct. 10, 2013, and entitled "Cooling Gel Pad," both of which are incorporated by reference herein in their entireties, disclose seats or pads that may be sat upon, but that are not aimed at scrotal cooling, nor do they exhibit cooling properties and temperatures optimal to improving male fertility.

Unlike these known devices, embodiments of the inventive fertility-enhancing cooling seat and related methods described herein provide convenient, optimized solutions to improve male fertility, including improving sperm morphology and motility.

In one embodiment, a fertility-enhancing cooling seat with a plurality of isolated cooling cells for lowering temperatures of human testicles so as to increase sperm quality and quantity, comprises: a top flexible portion including a plurality of cooling-cell top portions and a base portion extending between the cooling-cell top portions; a bottom flexible portion coupled to the top flexible portion, the bottom flexible portion forming a seal with the flat, web-like base portion, portions of the bottom flexible portion forming a plurality of cooling-cell bottom portions, such that each cooling-cell top portion of the plurality of cooling-cell top portions in combination with a cooling-cell bottom portion defines an isolated cooling-cell volumetric space, and the plurality of cooling-cell top portions in combination with the plurality of cooling-cell bottom portions define a plurality of isolated cooling-cell volumetric spaces; a phase-change material located in the plurality of cooling-cell volumetric spaces, the phase-change material configured to change from a solid phase to a liquid phase at a first temperature and that is configured to change from a liquid phase to a solid phase at a second temperature that is lower than the first temperature; wherein the phase-change material, plurality of cooling-cell top portions and the plurality of cooling-cell bottom portions form the plurality of isolated cooling cells, and at least one of the plurality of isolated cooling cells defines a diameter that is larger than a diameter of the other of the plurality of isolated cooling cells, and defines a volumetric space for PCM that is at least twice as large as the other of the plurality of isolated cooling cells.

An embodiment of the disclosure also includes a method of improving human sperm quantity and quality, that comprises: placing a cooling seat that includes a plurality of cooling cells, each cooling cell including a phase-change material, on a seating surface in an environment defining an ambient temperature; positioning testicles adjacent a large-diameter cooling cell of the plurality of cooling cells, the large-diameter cooling cell defining a cooling cell diameter that is larger than a diameter of the other cooling cells of the plurality of cooling cells; maintaining the testicles adjacent the large-diameter cooling cell for a first duration that is in a range of one to two hours, thereby causing heat of the testicles to be absorbed by the cooling seat, including the large-diameter cooling cell, causing at least a portion of the phase-change material to change from a solid to a liquid;

causing the testicles to be removed to a position that is not be adjacent to the large-diameter cooling cell for a second duration, thereby exposing the cooling seat to the ambient temperature; and maintaining the cooling seat at the ambient temperature, thereby causing the liquid of the phase-change material to change to a solid.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
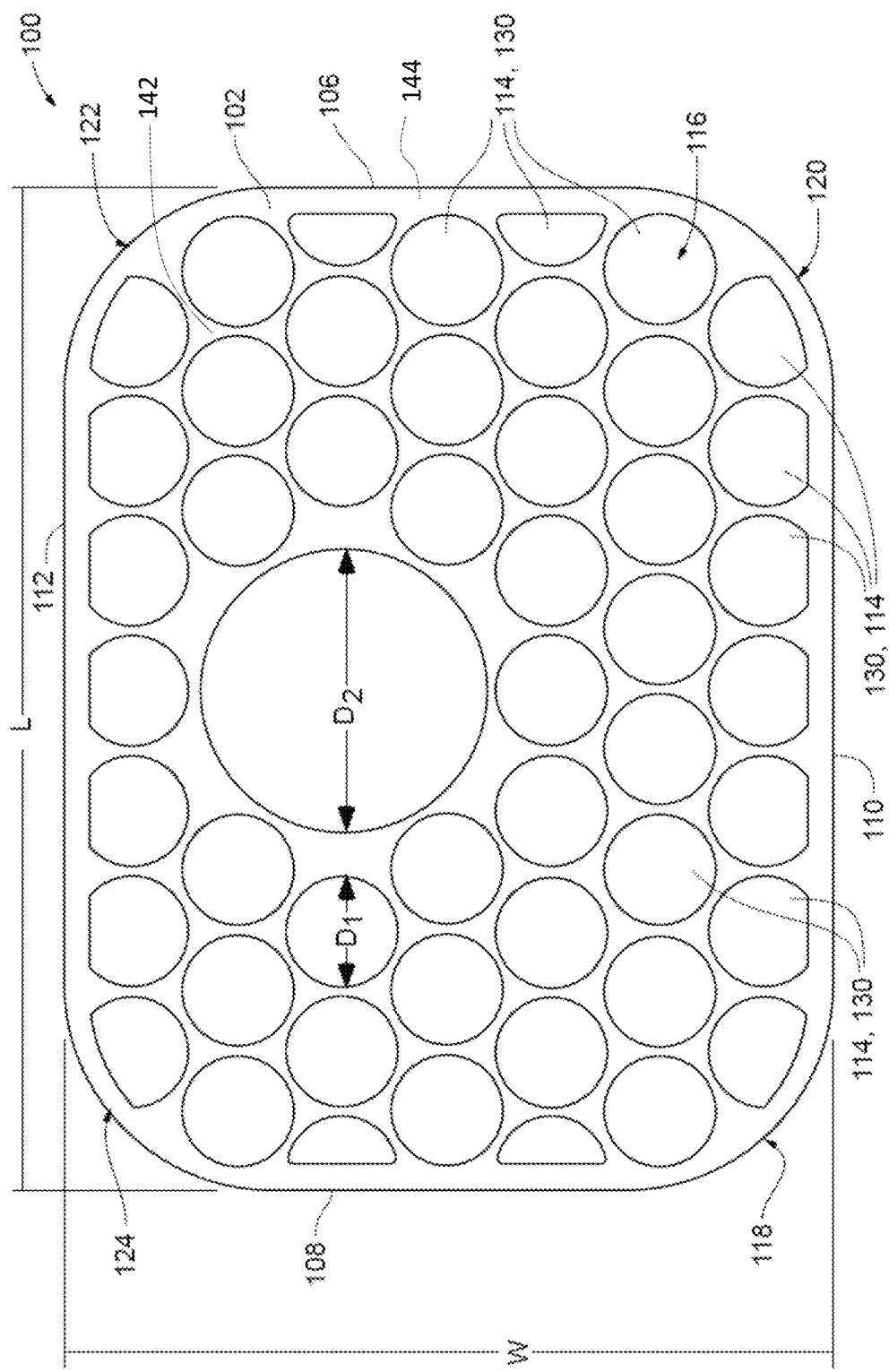
FIG. 1 is a top view of a cooling seat, according to an embodiment of the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

Figure 2:
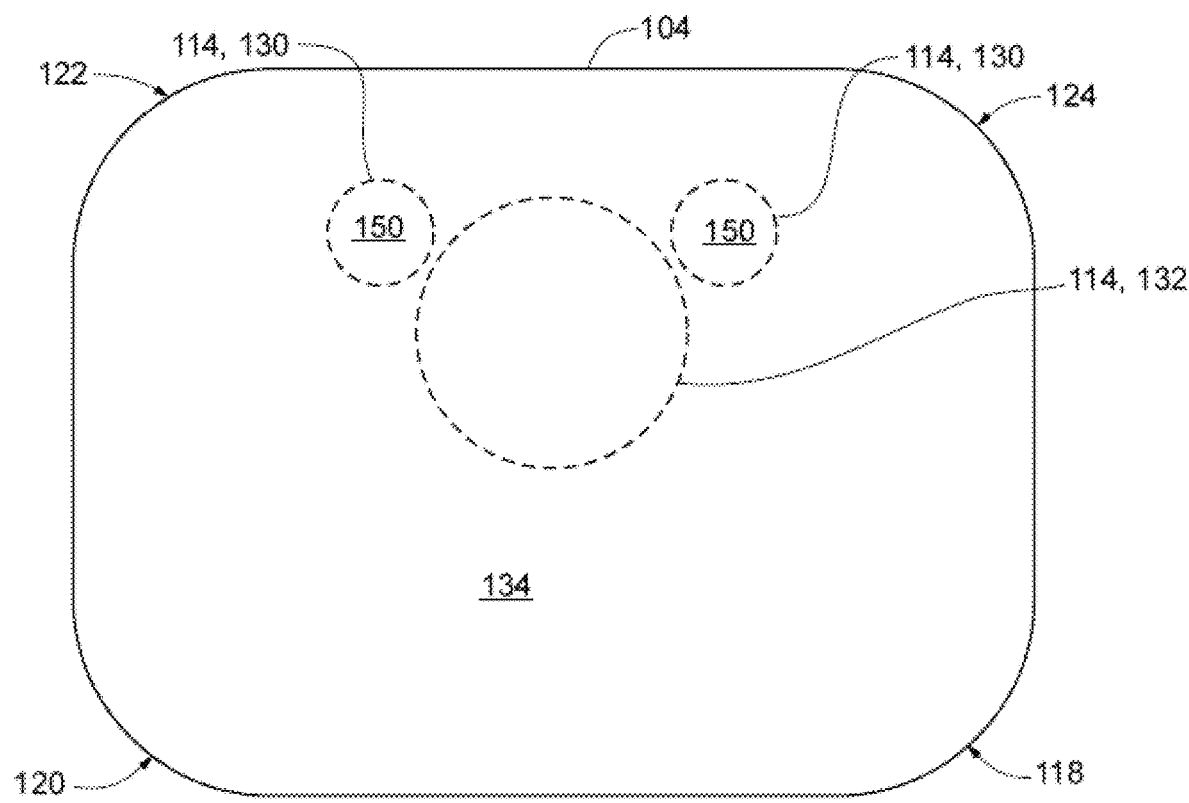
FIG. 2 is a bottom view of the cooling seat of FIG. 1.
Figure 3:
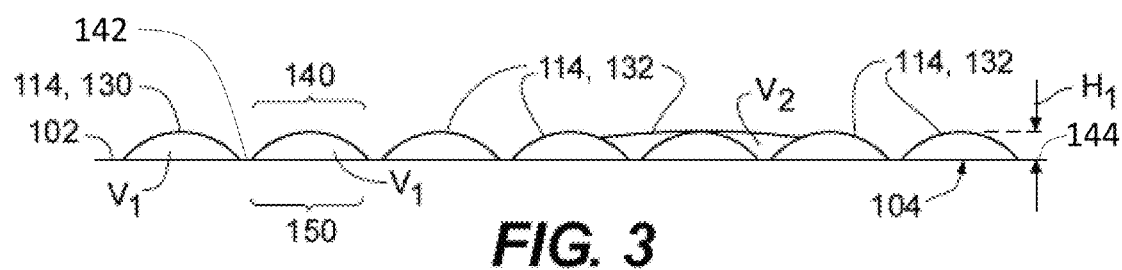
FIG. 3 is a right-side view of the cooling seat of FIG. 1 with a large cooling cell having a height that is substantially the same as the smaller-diameter, adjacent cooling cells, according to an embodiment of the disclosure.

Referring to FIGS. 1-3, an embodiment of fertility-enhancing cooling 100 seat for human males is depicted. FIG. 1 is a top view of cooling seat 100, FIG. 2 is a bottom view of cooling seat 100, and FIG. 3 is a side view of cooling seat 100.

Referring specifically to FIGS. 1 and 2, in an embodiment, cooling seat 100 includes top portion 102, bottom portion 104, front edge 106, rear edge 108, left-side edge 110, right-side edge 112 and a plurality of cooling cells 114 filled with fertility-optimized phase-change material (PCM) 116.

In an embodiment, Top portion 102 and bottom portion 104 may each comprise a flexible material, such as a polymer material, and may be joined together at multiple points to form the space that defines the plurality of cooling cells 114, as is described further below. In an embodiment, each of top portion 102 and bottom portion 104 may comprise a single layer of material, or may comprise multiple layers of materials.

In an embodiment, top portion 102 and bottom portion 104 comprise medical-grade tri-polymer materials. In an embodiment, top portion 102 and bottom portion 104 comprise a flexible polymer material having a thickness that is in a range of 0.010 mm to 0.100 mm. Those of ordinary skill will immediately appreciate that all ranges and values between the explicitly stated bounds are contemplated, e.g., from 0.010 mm to 0.050 mm, from 0.010 mm to 0.030, from 0.010 mm to 0.020 mm. In an embodiment, a layer of the material of the top and/or bottom portion is 0.014 mm thick. Generally thicker layers increases durability of top and bottom portions 102, 104, but generally thinner layers improves conformability of the seat, which may provide improved comfort to a user.

Embodiments of the material of top portion 102 and/or bottom portion 104 exhibit good resilience, high temperature flexibility, and excellent hydrolytic stability. In an embodiment, an anti-microbial material is added to the flexible polymer material. In an embodiment, the material of portions 102 and/or 104 may be weldable.

In an embodiment, the flexible polymer material of top portion 102 and/or bottom portion 104 may comprise a polyurethane material. In one such embodiment, the flexible polymer material may comprise or consist of an aromatic polyether polyurethane material. In an embodiment, the aromatic polyether polyurethane material may exhibit one, some, or all of the properties of the material described in Table 1 below:

TABLE 1

| | Test Values | Test Method ASTM |
|---|---|---|
| Durometer | 82A | D 2240 |
| Specific Gravity | 1.10 | D 792 |
| Elongation @ Break Elast | 660% | D 412 |
| Tensile Str. @ Break Elast | 5,080 psi | D 412 |
| 100% modulus | 725 psi | D 412 |
| 300% modulus | 1,100 psi | D 412 |
| Tear Strength Die C (lb/in) | 430 lb/in | D 624 |
| Abrasion Loss | 20 mm$^3$ | DIN 53.516 |
| Melt Range | 320-340° F. (160-170° C.) | |

Such properties include a durometer of 82 A, specific gravity of 1.10, elongation at break of 660%, tensile strength at break of 5,080 psi, 100% modulus at 725 psi, 300% modulus at 1,100 psi, and a melt range of 160° C. to 170° C.

Bottom layer 104, in an embodiment, may also comprise an outer layer over the flexible polymer material, such as a fabric or other material. A fabric layer, or other such external layer or covering, may be more pleasing to the touch of a user, and may also increase friction between cooling seat 100 and the surface that it is placed upon.

In an embodiment, and as depicted, cooling seat 100 may generally define a rectangular shape with a length L, a width W, and having four corners, 118, 120, 122 and 124. In an embodiment, corners 118-124 may be rounded for ease of handling by a user and for ease of placement onto a surface such as a chair seat, stool, bench, or other surface onto which cooling seat 100 may be placed. In other embodiments, cooling seat 100 may define other shapes, such as a circle, oval, square, or other such shape configured for ease of handling and fitment onto a particular seating surface.

Referring specifically to FIG. 1, in an embodiment, and as depicted, the plurality of cooling cells 114 may include a plurality of different-sized and different-shaped cooling cells 114.

In and embodiment, as viewed in a direction from top to bottom, each cooling cell 114 may generally define a circular shape, though in other embodiments, cooling cells 114 may define other shapes, such as ovals, squares, rectangles, hexagons, octagons and so on. Circular and oval shapes may provide some additional advantages in reducing or eliminating cell edges that could potentially cause discomfort to a user, while also simplifying the manufacturing process.

As also depicted, the shape of an individual cooling cell 114 may vary based on position of the cooling cells 114 relative to the edges of the cooling seat. Depending on the particular arrangement of cooling cells 114, cooling cell size, density, and overall cooling seat dimensions, those cooling cells 114 adjacent edges 106-112 may be truncated shapes or partial shapes as compared to interior cooling cells (those not adjacent edges 106-112), so as to fit within the confines of cooling seat 100. As depicted, a majority of cooling cells 114 adjacent edges 106-112 define shapes formed of partial circles, such as, for example, cooling cells 114*a* and 114*b*.

In an embodiment, the plurality of cooling cells 114 may comprise one or more sizes. In this context, size may refer firstly to diameter as measured laterally, in a horizontal plane (length×width plane). Size may also refer to cooling cell height as measured vertically, with some cooling cells having a larger height than others, in certain embodiments (see also FIG. 3 depicting a cell height H).

Referring to FIGS. 5A to 9B, various embodiments of cooling cells 114, defining various shapes, are depicted.

Figure 5A:
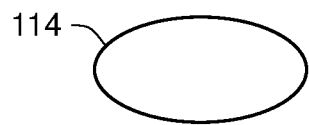
FIG. 5A is a top view of a cooling cell having an elliptical or oval shape, according to an embodiment of the invention.
Figure 5B:
FIG. 5B is a side view of the cooling cell of FIG. 5B.
Figure 6A:
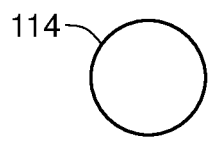
FIG. 6A is a top view of a cooling cell having a circular shape, according to an embodiment of the invention.
Figure 6B:
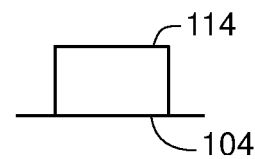
FIG. 6B is a side view of the cooling cell of FIG. 6B.

FIG. 5A is a top view of a cooling cell 114 that defines an oval shape; FIG. 5B is a side view of the cooling cell 114 of FIG. 5A, the cooling cell having a dome shape in the side view. FIG. 6A is a top view of a cooling cell 114 that defines a circle; FIG. 6B is a side view of the cooling cell 114 of FIG. 5A, which in this embodiment defines a square in the side view.

Figure 7A:
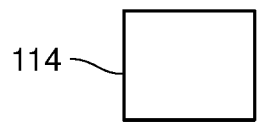
FIG. 7A is a top view of a cooling cell having a square shape, according to an embodiment of the invention.
Figure 7B:
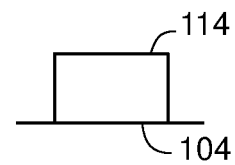
FIG. 7B is a side view of the cooling cell of FIG. 7B.

FIG. 7A is a top view of a cooling cell 114 that defines a square; FIG. 6B is a side view of the cooling cell 114 of FIG. 7A, which in this embodiment defines a square in the side view.

Figure 8A:
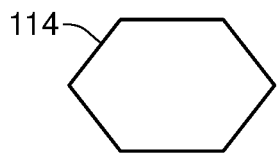
FIG. 8A is a top view of a cooling cell having a hexagonal shape, according to an embodiment of the invention.
Figure 8B:
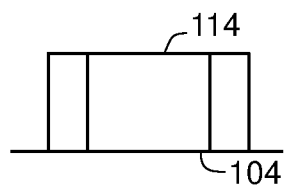
FIG. 8B is a side view of the cooling cell of FIG. 8B.

FIG. 8A is a top view of a cooling cell 114 that defines a hexagon; FIG. 8B is a side view of the cooling cell 114 of FIG. 8A.

Figure 9A:
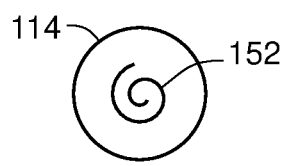
FIG. 9A is a top view of a cooling cell having a circular shape, and having additional top structure, according to an embodiment of the invention.
Figure 9B:
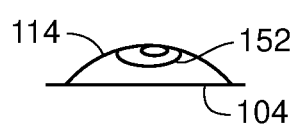
FIG. 9B is a side view of the cooling cell of FIG. 9B.

FIG. 9A is a top view of a cooling cell 114 that defines a circle; FIG. 9B is a side view of the cooling cell 114 of FIG. 9A. In this embodiment, cooling cell 114 is shaped substantially the same as cooling cells 114 of the embodiment depicted in FIGS. 1 and 3. However, in the embodiment of FIGS. 9A and 9B, cooling cell 114 includes additional structure 152 on a top portion of cooling cell 114. Structure 152 may comprise grooves, channels, or raised portions. Such structure 152 may be helical, as depicted, may be otherwise curved, or may alternatively, comprise one or more linear portions.

Referring again to FIG. 1, in the embodiment depicted, the plurality of cooling cells 114 includes first-sized cooling cells 130 and one or more second-sized cooling cells. In this embodiment, the plurality of cooling cells 114 includes only one second-sized cooling cell 132, which is larger than any of the first-sized cooling cells 130. As explained further below, second-, and larger-sized cooling cell 132 may be a target cooling cell which is intended to be targeted or placed directly below a male scrotum of a user, so as to maximize a volume of cooling PCM 116 directly at the testicles. For the sake of simplicity, hereinafter, first-sized cooling cells 130 will generally be referred to as small cooling cells 130, and second-sized cooling cells 132 will generally be referred to as large cooling cells 132, though it will be understood that first- and second-sized cooling cells may comprise any number of different size relationships as described above and herein.

Small cooling cells 130 define a diameter $D_1$ that is smaller than a diameter $D_2$ of second-sized cooling cell 132. The ration of $D_2$ to $D_1$ may vary, depending on a number of factors, such as desired diameter $D_2$ and/or volume of cooling cell 132, desired density of cooling cells 114, and so on. In the embodiment depicted, $D_2$ is approximately 2.5 times larger than $D_1$. In another embodiment, $D_2$ is 2 to 3 times larger than $D_1$; in another embodiment, the ratio of $D_2$ to $D_1$ is in the range of 1.5 to 5.

In an embodiment, all of, or a majority of, cooling cells 114 may generally be equidistantly spaced from one another, and in particular, second-sized cooling cells 130, such that a minimum distance from one cooling cell 114 to another cooling cell 114 is the same or approximately the same. Equidistant spacing provides the advantage that a user may sit on any portion of cooling seat 100 and receive a cooling effect.

Referring also to FIG. 3, top portion 102 of cooling seat 100 includes a plurality of cooling-cell top portions 140 and base portion 142. Base portion 142, in an embodiment, comprises a generally flat, web-like portion that is between cooling cells 114, and generally flat border area 144 that extends circumferentially about the perimeter of top portion 102, and along edges 106-112. Top surface 146 of top portion 102 is comprised of surfaces of cooling-cell top portions 140 and surfaces of base portion 142. As such, in an embodiment, top surface 146 is a contoured surface defined by a plurality of "bumps" (cooling cells 114) extending from a substantially flat surface.

Referring to FIGS. 2 and 3, in the embodiment depicted, bottom portion 104 is depicted. For the sake of understanding, several cooling cells 114 are depicted in dashed lines in FIG. 2. Bottom portion 104 of cooling seat 100 comprises a substantially flat, planar portion, and defines bottom surface 134. In this embodiment, bottom portion and bottom surface 134 are continuous and substantially flat. In other embodiments, bottom portion 104 may be contoured, or even include portions of cooling cells 114 that extend vertically, transversely or perpendicularly, in a direction away from bottom surface 134, in a manner similar to that of top portion 102. In one such embodiment, not depicted, bottom portion 104 is substantially the same as top portion 102, and includes portions of vertically-extending cooling cells 114. In such an embodiment, a user may sit on either top portion 102 or bottom portion 104 and be in contact with vertically-extending cooling cells 114.

In an embodiment, bottom portion 104 may be covered by, or coated with, a finishing material or coating. Such a covering or coating may make cooling seat 100 more pleasing to the touch of a user, and/or may provide an outer surface having a higher coefficient of friction so as to prevent sliding of cooling seat 100 on the surface receiving the cooling seat. In an embodiment, the covering or coating may comprise a "velvet" material, or other material that is soft to the touch, and fabric-like. In other embodiments, the coating may comprise a rubber-like material to enhance grip of cooling seat 100 with the surface receiving the cooling seat. In alternative embodiments, both top portion 102 and bottom portion 104 may be coated with such a covering or coating.

Each cooling cell 114 defines a height. In the embodiment depicted in FIG. 3, each of cooling cells 130 and 132 has a same height $H_1$.

Figure 4:
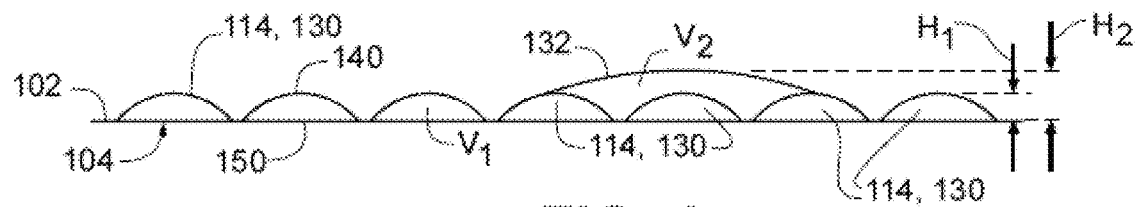
FIG. 4 is a right-side view of the cooling seat of FIG. 1 with a large cooling cell having a height that is larger as compared to the smaller-diameter, adjacent cooling cells, according to an embodiment of the disclosure.

In alternate embodiments, a height of a cooling cell 114 may not be the same for all of the cooling cells 114 of the cooling seat. In one such embodiment, as depicted in FIG. 4, large cooling cell 132 has a height $H_2$ that is larger than a height $H_1$. The larger height $H_2$ enables a larger volume of PCM 116 to be used in cooling cell 114, such that a larger amount of PCM 116 may be placed adjacent the scrotum and testicles of a user. The larger height $H_2$ may also cause cooling cell 132 to be placed between the legs of a user and at a height that extends upwardly between the legs and therefore closer to the scrotum and testicles of the user.

Referring again to FIG. 3, in an embodiment, each cooling cell 114 is separate and distinct from the other in that each cooling cell 114 defines an isolated cooling cell volume V (V1 for first-sized cooling cells 130 and V2 for second-sized cooling cells 132). In such an embodiment, none of cooling cells 114 are in fluid communication with another cooling cell 114. This can be seen in FIG. 2 which depicts small cooling cells 130 in side view. For each cooling cell 114, including cooling cells 130 and 132, the volume V is defined by, and bounded by, a cooling-cell top portion 140 and a cooling-cell bottom portion 150. In this embodiment, each cooling-cell bottom portion 150 is part of, or a portion of, the larger bottom portion 104. Together, each cooling-cell bottom portion 150 combined with a cooling-cell top portion 140 forms an isolated cooling-cell volumetric space to be filled by PCM 116 to form cooling-cells 114.

A ratio of volume V2 (large) to volume V2 (small) may vary depending on the desired size and cooling capacity desired, and in particular the size and capacity of second- or large-sized cooling cells 132, which are intended to be closest to the testicles. In an embodiment, volume V2 is in the range of two to ten times larger than volume V1; in another embodiment a ration of V2 to V1 is in the range of three to five.

Referring also to FIG. 1, when cooling seat 100 is in finished form (after manufacture) base portion 142 of top portion 102, which includes the portions between cooling cells 114, is in direct contact with, or even merged with, bottom portion 102, and may form a seal between top portion 102 and bottom portion 104, thereby isolating cooling cells 114 from one another.

In a manufacturing method according to the claimed invention, top portion 102 is placed into a top mold having multiple cavities corresponding to the plurality of cooling cells 114, bottom portion 104 is placed into a bottom mold, PCM 116 is injected between top portion 102 and bottom portion 104, filling the cavities lined with top portion 102. The top mold and the bottom mold are coupled together, causing base portion 142 of top portion 102 to contact bottom portion 104. Base portion 142 is then sealed to bottom portion 104 by applying heat or by other means, such as radio-frequency (RF) welding or bonding. The connection or coupling of a part of top portion 102 to bottom portion 104 seals off the cooling cells 114 from one another. In an optional step, exterior surface 134 of bottom portion 104 may be coated with a finishing material.

Unlike commonly-used gels or phase-change materials found in cooling garments, wraps, cushions and the like, used to cool parts of the human body, fertility-optimized PCM 116 is specifically formulated to maintain a target temperature $T_L$ for an extended period of time, and to relatively-quickly revert back to solid form at a temperature $T_S$, which is at or above room temperature, so as to avoid refrigeration. Target temperature $T_L$ is the temperature maintained by PCM 116 as it absorbs heat from the human body, and is the temperature at which PCM 116 changes phase from a solid to a liquid. Unlike ice or many known gels that start at a very low temperature, target temperature $T_L$ is relatively high, and relatively close to body temperature, so as to provide a gentle and effective cooling of the scrotum and other tissues. The relatively higher temperature $T_L$ also allows a user to engage with cooling seat 100 for relatively longer periods of time than would otherwise be possible. Temperature $T_S$ is the temperature at which PCM 116 reverts from a liquid phase back to a solid.

Target temperature $T_L$, is below the human body temperature of 37° C. (98.6° F.) so as to achieve a cooling effect. As described briefly above, it is understood that maintaining sperm at a temperature of 2° C.-4° C. below body temperature is ideal. Consequently, in an embodiment, target temperature $T_L$ is in the range of 25° C. to 36° C. Those of ordinary skill will immediately appreciate that all ranges and values between the explicitly stated bounds are contemplated, e.g., from 27° C. to 35° C., 30° C. to 36° C., and from 33° C. to 35° C.

However, through experimentation, Applicants have discovered that using a specific target temperature $T_L$ that is significantly lower than body temperature, such as 25.6° C. (78° F.), produces better-than-expected sperm quantity and quality, in part due to thermal losses. This is particularly true when a user is wearing clothing, typically a first layer which is an undergarment, and a second layer which is a pair of pants, while sitting on cooling seat 100, which insulates the testicles during use, and requires a lower target temperature $T_L$ for PCM 116 for optimum effectiveness. Lowering the temperature of the scrotum and contents by even 0.5° C.-1° C. is determined to be beneficial. At the same time, target temperature $T_L$ is not so low that it is uncomfortable to a user, which could result in the user not consistently using cooling seat 100.

Consequently, in an embodiment, target temperature $T_L$ may be much lower than 2° C. to 4° C. below body temperature, and rather, may be in a range of 24° C. to 28° C. In other embodiments, target temperature T may be in a range of 25° C. to 27° C. Target temperature T may be selected based on expected thermal losses which may account for expected layers of clothing and expected environmental or room temperature. In some embodiments, room temperature is expected to be in the range of 19° C.-22° C. (approximately 69° F.-72° F.). Lowering the temperature of the scrotum and contents by even 0.5° C.-1° C. is determined to be beneficial.

As will be described further below, an advantage of fertility-optimized PCM 116 and cooling seat 100 is that a user does not have to refrigerate cooling seat 100 with PCM 116 in order for it to "recharge" or convert back to solid form. This is because temperature $T_S$ is at or above the expected ambient temperature in which cooling seat 100 is used. As such, when the higher-temperature human body is not in contact with cooling seat 100, and thereby absorbing body energy and converting to a liquid phase, PCM 116 releases energy to the environment, causing its temperature to lower to $T_S$ or below, which in turn causes PCM 116 convert back to solid form or "phase", i.e., PCM 116 and cooling seat 100 "recharge" at ambient or room temperature.

Such a feature is advantageous in that each time a user disengages from cooling seat 100 for any reason, such as taking a lunch break during the workday, and so on, PCM 116 will automatically begin to recharge, without any action being required from the user. Such a feature encourages regular, repeated use, which greatly improves the chances of improving fertility.

In an embodiment, PCM 116 maintains target temperature $T_L$ for a duration D of approximately 4 hours, which, in an embodiment, is a maximum expected time that a user would be expected to use cooling seat 100 in a single use. In some embodiments, duration D may be in the range of 2 to 4 hours, dependent on the size of cooling seat 100, and target temperature $T_L$. A higher target temperature will reduce the amount of heat absorbed by PCM 116 and increase duration D. The overall volume and mass of PCM 116 used in cooling seat 100 also affects the duration D, with larger cooling seats 100 having a longer duration D as compared to smaller seats 100. In an embodiment, cooling seat 100 and/or PCM 116 has a duration D that is in a range of 1 to 3 hours, or in a range of 2 to 4 hours. Unlike known PCM-based cooling apparatuses that include gels and PCMs that change phase at low temperatures, for example, 59° F., to maximize cooling rates, and that subsequently have low durations, PCM 116 is designed to maintain a low-temperature difference for a longer duration.

The time to recharge, or change phase from liquid to solid, after use, depends on ambient temperatures. In an embodiment, the amount of time required to recharge is approximately the same as duration D. In an embodiment, a recharge time is approximately 4 hours at room temperature, which in an embodiment is 70° F. In an embodiment, a recharge time is in the range of 2-4 hours at room temperature, which in an embodiment is 70° F. Recharge times may be reduced very quickly if cooling seat 100 is placed in a cool environment, such as a refrigerator.

In the embodiments described above, PCM 116 converts to a solid without refrigeration because temperature $T_S$, the temperature at which PCM 116 converts from a liquid back to a solid, is above expected ambient temperature, and target temperature $T_L$ is at an even higher temperature. In alternate embodiments, cooling seat 110 may include a PCM 116 exhibiting a conversion temperature $T_S$ that is below expected ambient temperature, such that cooling seat 100 that would require refrigeration, or other exposure to a below-ambient temperature environment after use. Such embodiments may include a PCM 116 having a temperature $T_S$ that is in the range of 15° C. to 21° C. Those of ordinary skill will immediately appreciate that all ranges and values between the explicitly stated bounds are contemplated, e.g., from 16° C. to 20° C., 18° C. to 19° C., and so on. In an embodiment $T_S$ is approximately 18° C. In such embodiments requiring refrigeration to achieve a temperature $T_S$ that is below ambient or room temperature, target temperature $T_L$ may or may not be adjusted generally downward. In an embodiment wherein $T_S$ is below ambient temperature, such as in the range of 15° C. to 21° C., $T_L$ may still be in the range of 25° C. to 36° C., though in other embodiments, $T_L$ may still be in a lower range of 22° C. to 36° C., or in sub-ranges that include 22° C. to 30° C., and 24° C. to 28° C.

One of ordinary skill in the art would also understand that the invention contemplates adjustments to duration of use and the recognized trade-off of having to use a refrigerator or other cooling device to recharge and restore the cooling power of fertility-enhancing cooling seat 100. User comfort and usage compliance may also be trade-offs that would need to be accounted for in a usage protocol, such as the protocols, methods and treatments described in further detail below.

In an embodiment, PCM 116 comprises an alkane phase-change material. n-Alkanes and their blends are characterized as phase change materials (PCMs) due to their superior thermodynamic performances, for storing thermal energy. Paraffin as a Phase Change Material (PCM) as detailed by A. Vakhshouri (reviewed: Nov. 14, 2019, published: Dec. 15, 2019 DOI: 10.5772/intechopen.90487), and incorporated herein by reference, provides a detailed descriptions of embodiments of PCM 116.

As will be understood by those of ordinary skill in the art, PCM materials store energy in the form of latent heat at constant temperature during phase transition. These materials are classified into three categories: organic, inorganic and eutectics. PCM 116 may also comprise materials in any of these three categories or organic, inorganic and eutectics. While various types of material could be used in the design of fertility-enhancing cooling-seat 100, each category and type of material provides different properties and provides different benefits and trade-offs from a perspective of performance, design, cost and efficacy.

In an embodiment, PCM 116 comprises an organic material. In one such embodiment, PCM 116 comprises paraffin, the use of which provides numerous advantages. Organic PCMs, including paraffin, generally show no change in performance or structure (e.g., phase separation) over numerous phase-change cycles. In addition, supercooling phenomena cannot be observed in organic PCMs. The classification of organic PCMs is unique. This division is mainly based on their application contexts. In general, they are classified into two major paraffin and non-paraffin sections.

In an embodiment, PCM 116 comprises a non-paraffin organic PCM. Non-paraffinic organic PCMs are known to be the most widely used families. In addition to their different properties compared to paraffins, they have very similar properties to each other. Researchers have used various types of ether, fatty acid, alcohol, and glycol as thermal energy storage materials. These materials are generally flammable and less resistant to oxidation. Although non-paraffin organic PCMs have high latent heat capacity, they have weaknesses such as flammability, low thermal conductivity, low combustion temperatures, and transient toxicity. Embodiments of PCM 116 that comprise non-paraffin organic material include fatty acids, glycols, polyalcohols, and sugar alcohols.

In an embodiment, PCM 116 comprises a paraffin organic PCM. In such an embodiment, PCM 116 comprises a mixture of straight-chain n-alkanes with the general formula CH3-(CH2)n-CH3. However, in some cases, paraffin is used as another name for alkanes. According to Gulfam R. et al., paraffins may be classified based on the number of carbon atoms as well as their physical states. See Gulfam R, Zhang P, Meng Z, Advanced Thermal Systems Driven by Paraffin-Based Phase Change Materials-A Review, Applied Energy, 2019, 238:582-611, the entire article being incorporated herein by reference in its entirety.

According to this classification, at room temperature, 1-4 numbers of carbons refer to pure alkanes in a gas phase, 5-17 carbons are liquid paraffins, and more than 17 is known as solid waxes. These waxy solids refer to a mixture of saturated hydrocarbons such as linear, iso, high branched, and cycloalkanes. Generally, paraffin-based PCMs are known as waxy, solid paraffins. Embodiments of PCM 116 may include paraffins with or without one or more isomers. Such embodiments may exhibit a range of melting temperatures. Embodiments of PCM 116 may include various mixtures of isomers with the paraffin to facilitate a desired range of melting temperatures, i.e., target temperature $T_L$.

Paraffins, including embodiments of PCM 116, typically have high latent heat capacity. If the length of the chain increases, the melting ranges of waxes also increase, while the latent heat capacity of melting is not subject to any particular order. Table 2 below describes the various melting points of different PCM 116 materials.

TABLE 2

Thermophysical Properties of n-Paraffins and Commercial Paraffinic PCMs 116

| Materials | Melting point (° C.) | Latent heat (kJ/kg) | Density* (kg/m$^3$) | Thermal conductivity** (W/mK) |
|---|---|---|---|---|
| n-Tetradecane (C$_{14}$) | 6 | 228-230 | 763 | 0.14 |
| n-Pentadecane (C$_{15}$) | 10 | 205 | 770 | 0.2 |
| n-Hexadecane (C$_{16}$) | 18 | 237 | 770 | 0.2 |
| n-Heptadecane (C$_{17}$) | 22 | 213 | 760 | 0145 |
| n-Octadecane (C$_{18}$) | 28 | 245 | 865 | 0.148 |
| n-Nonadecane (C$_{19}$) | 32 | 222 | 830 | 0.22 |
| n-Eicosane (C$_{20}$) | 37 | 246 | | |
| n-Henicosane (C$_{21}$) | 40 | 200, 213 | 778 | |
| n-Docosane (C$_{22}$) | 44.5 | 249 | 880 | 0.2 |
| n-Tricosane (C$_{23}$) | 47.5 | 232 | | |
| n-Tetracosane (C$_{24}$) | 52 | 255 | | |
| n-Pentacosane (C$_{25}$) | 54 | 238 | | |
| n-Hexacosane (C$_{26}$) | 56.5 | 256 | | |
| n-Heptacosane (C$_{27}$) | 59 | 236 | | |
| n-Octacosane (C$_{28}$) | 64.5 | 253 | | |
| n-Nonacosane (C$_{29}$) | 65 | 240 | | |
| n-Triacontane (C$_{30}$) | 66 | 251 | | |
| n-Hentriacontane (C$_{31}$) | 67 | 242 | | |
| n-Dotriacontane (C$_{32}$) | 69 | 170 | | |
| n-Triatriacontane (C$_{33}$) | 71 | 268 | 880 | 0.2 |
| Paraffin C$_{16}$-C$_{18}$ | 20-22 | 152 | | |
| Paraffin C$_{13}$-C$_{24}$ | 22-24 | 189 | 900 | 0.21 |
| RT 35 HC | 35 | 240 | 880 | 0.2 |
| Paraffin C$_{16}$-C$_{28}$ | 42-44 | 189 | 910 | |
| Paraffin C$_{20}$-C$_{33}$ | 48-50 | 189 | 912 | |
| Paraffin C$_{22}$-C$_{45}$ | 58-60 | 189 | 920 | 0.2 |
| Paraffin C$_{21}$-C$_{50}$ | 66-68 | 189 | 930 | |
| RT 70 HC | 69-71 | 260 | 880 | 0.2 |
| Paraffin natural wax 811 | 82-86 | 85 | | 0.72 (solid) |
| Paraffin natural wax 106 | 101-108 | 80 | | 0.65 (solid) |

*At 20° C.
**Just above melting point (liquid phase).

In general, paraffin waxes are safe, reliable, inexpensive, and non-irritating substances, and relatively obtained in a wide range of temperatures. As far as economic issues are concerned, most technical grade waxes can be used as PCMs in latent heat storage systems. From the chemical point of view, paraffin waxes are inactive and stable. They exhibit moderate volume changes (10-20%) during melting but have low vapor pressure.

The paraffin based PCMs 116 usually have high stability for very long crystallization-melting cycles. In an embodiment, PCM 116 for use in fertility-enhanced cooling seat 100 may comprise or consist of n-Hecadecane (C16), n-Heptacecane (C17), n-Otadecane (C18) and n-Nonadecane (C19). Blends can also be made from these preferred PCMs to achieve the desired temperature outcomes. Benefits for achieving the desired cooling effects are independent of the PCM source albeit petroleum, plant or any synthetic process.

As described briefly above, in general use, cooling seat 100 may be placed on a surface, then sat upon by a user. Cooling seat 100 is positioned such that at least some of cooling cells 114 are positioned directly below, and adjacent to, the scrotum and testicles of the user. The cooling seat 100 is left in place for a period of time, contact duration Dc, which may be predetermined, and which may be repeated such that cooling cells 114 with PCM 116 lower the temperature of the scrotum and testicles a desired amount, which as described above, may range from 0.5° C. to up to 4° C. below body temperature of 37° C. When using the embodiment of FIG. 1, which includes small cooling cells 130 and a large cooling cell 132, a user takes the additional step of positioning large cooling cell 132 directly below the scrotum.

Consequently, embodiments of the invention include methods of treatments for lowering sperm temperature, including the use of a cooling device, apparatus or seat to increase human sperm quantity and quality.

Figure 10:
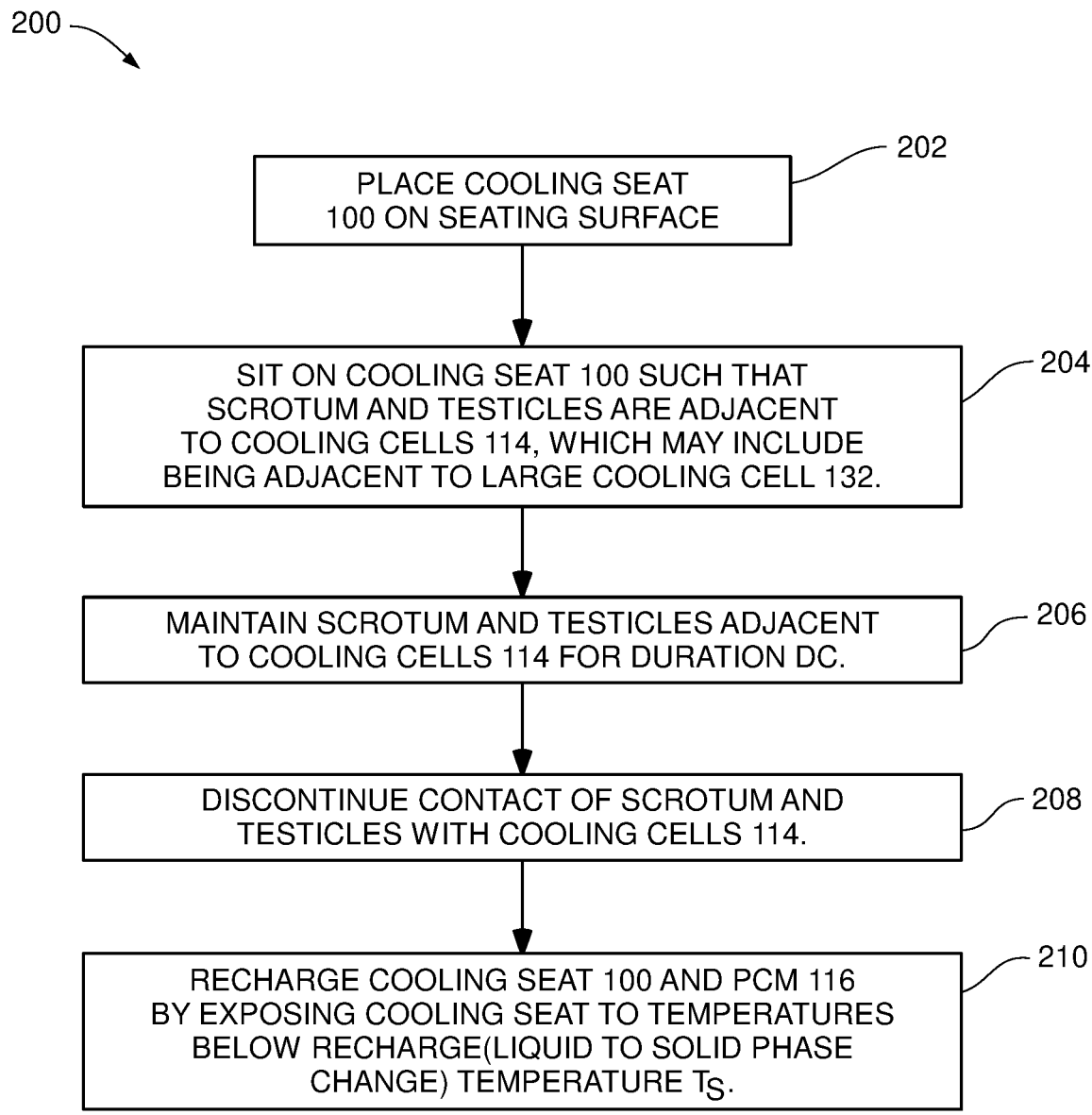
FIG. 10 is a flow diagram of a method of treatment for lowering sperm temperature through use of a cooling seat, according to an embodiment of the invention.

FIG. 10 depicts an embodiment of a method 200 of treatment that includes using cooling device 100 to lower a temperature of human tissue, including a human scrotum and testicles, so as to increase sperm quantity and quality. At Step 202, a user places cooling seat 100 on a surface, such as a chair, bench, stool, the ground, and so on. At Step 204, the user sits on cooling seat 100 such that the user's scrotum and testicles are positioned above, and adjacent to (with or without clothing between), cooling cells 114. Step 204 may also include causing the user's scrotum and testicles to be positioned above a cooling cell 132 that is larger than the other cooling cells 130. At Step 206, a user maintains the scrotum and testicles in position adjacent one or more of cooling cells 114 for a contact duration Dc, while PCM 116 absorbs heat from the body of the user, including the scrotum and testicles, and changes phase from solid to liquid, thereby lowering the temperature of the scrotum, testicles and sperm therein.

In embodiments, contact duration Dc may comprise a continuous time, but in other embodiments, contact duration Dc may comprise multiple shorter durations, or sub-durations, that add together to form contact duration Dc. In an embodiment, contact duration Dc is in a range of 1 to 6 hours per day. In other embodiments, contact duration Dc is in a range of 2 to 4 hours per day or 1 to 2 hours per day. In an embodiment where contact duration Dc is not a continuous duration, Dc comprises two sub-durations per day, each sub-duration being period of time being approximately half the time of contact duration Dc; in another embodiment, Dc comprises three sub-durations per day, each sub-duration being approximately one third of contact duration Dc. In an embodiment, contact duration Dc is 4 hours per day, consisting of two 2-hour sub-durations or four 1-hour sub-durations, per day. Those of ordinary skill will immediately appreciate that all ranges and values between the explicitly stated bounds are contemplated.

At Step 208, after completion of duration Dc a user discontinues contact with cooling seat 100, such that the scrotum and testicles are not adjacent to cooling seat 100 or cooling cells 114. At Step 210, PCM 116 of cooling seat 100 recharges, or changes phase from liquid to solid through exposure of cooling seat 100 to a temperature that is below the temperature $T_S$ that causes PCM 116 to change from a liquid to a solid. Steps 206 and 208 may be repeated as desired.

In an embodiment, treatment 200 is repeated each day over a treatment period P. Treatment period P may be in a range of 10 to 120 days. Those of ordinary skill will immediately appreciate that all ranges and values between the explicitly stated bounds are contemplated, such as, 30 to 90 days, 60 to 90 days, and so on. In an embodiment treatment period P may be 90 days long. A human sperm production cycle is understood to be substantially 74 days, such that a treatment period P that is at least equal to an expected sperm production cycle, e.g., 74 days, may be advantageous.

Clinical studies by the inventors of the instant application show for the first time that the use of fertility-enhancing cooling seat 100 demonstrates efficacy associated with the cooling of scrotum and testicles resulting in improved sperm quantity and quality.

The study looked at men who were being evaluated for infertility. Patients provided a semen analysis. Patients were given a cooling seat 100 to use for 3 months and then evaluated for any improvements in semen quality. Target temperature $T_L$ of cooling seat 100 was approximately 77.5° F. The patients were instructed to sit on the seat for at least 2 hours per day. A total number of 3 patients completed the study.

Semen analyses were evaluated for sperm count, morphology, and motility. One patient's sperm count improved 11 million/ml to 26 million/ml. Patient 2 improved in morphology from 4% normal to 28% normal. The third patient showed no improvement in any criteria.

Data from the study demonstrates that by externally cooling the testicles patients using embodiments of cooling seat 100 will yield an improvement in sperm quality.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the spirit and scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A fertility-enhancing cooling seat with a plurality of isolated cooling cells for lowering temperatures of human testicles so as to increase sperm quality and quantity, comprising:
    a top flexible portion including a plurality of cooling-cell top portions and a base portion extending between the cooling-cell top portions;
    a bottom flexible portion coupled to the top flexible portion, the bottom flexible portion forming a seal with the base portion, portions of the bottom flexible portion forming a plurality of cooling-cell bottom portions, such that each cooling-cell top portion of the plurality of cooling-cell top portions in combination with a cooling-cell bottom portion defines an isolated cooling-cell volumetric space, and the plurality of cooling-cell top portions in combination with the plurality of cooling-cell bottom portions define a plurality of isolated cooling-cell volumetric spaces;
    a phase-change material located in the plurality of cooling-cell volumetric spaces, the phase-change material configured to change from a solid phase to a liquid phase at a first temperature and that is configured to change from a liquid phase to a solid phase at a second temperature that is lower than the first temperature;
    wherein the phase-change material, plurality of cooling-cell top portions and the plurality of cooling-cell bottom portions form the plurality of isolated cooling cells, and at least one of the plurality of isolated cooling cells defines a dimension that is larger than a dimension of another of the plurality of isolated cooling cells, wherein the dimension that is larger includes having a volumetric space for phase-change material that is at least twice as large as the other of the plurality of isolated cooling cells, and a height of the at least one of the plurality of isolated cooling cells that is larger than another of the plurality of isolated cooling cells is greater than a height of any other of the plurality of isolated cooling cells.

2. The fertility-enhancing cooling seat of claim 1, wherein the phase-change material is configured to change from a solid phase to a liquid phase at the first temperature that is below 37° C. and that is configured to change from a liquid phase to a solid phase at the second temperature that is at or above 19° C.

3. The fertility-enhancing cooling seat of claim 1, wherein the first temperature is approximately 78° F.

4. The fertility-enhancing cooling seat of claim 3, wherein the first temperature is in a range of 75° F. to 80° F., and the second temperature is in a range of 68° F. to 72° F.

5. The fertility-enhancing cooling seat of claim 1, wherein the phase-change material is an alkane phase-change material.

6. The fertility-enhancing cooling seat of claim 1, wherein the base portion of the top portion comprises a flat, web-like portion.

7. The fertility-enhancing cooling seat of claim 1, wherein the height of the at least one of the plurality of isolated cooling cells that defines a larger dimension is substantially located at a position that is equidistant to a front edge and a rear edge of the cooling seat, and is closer to a right edge of the cooling seat as compared to a left edge of the cooling seat.

8. The fertility-enhancing cooling seat of claim 1, wherein each of the plurality of isolated cooling cells forms a circular shape as viewed in a top to bottom direction, and the dimension that is larger than a dimension of another of the plurality of isolated cooling cells is a diameter of the at least one of the plurality of isolated cooling cells.

9. The fertility-enhancing cooling seat of claim 1, wherein each of the plurality of isolated cooling cells forms a shape as viewed in a top to bottom direction, the shape being one of a circle, hexagon, octagon, square, or oval.

10. The fertility-enhancing cooling seat of claim 1, wherein the phase-change material comprises paraffin.

11. The fertility-enhancing cooling seat of claim 10, wherein the phase-change material comprises paraffin having a first melting temperature and an isomer having a second melting temperature, wherein the second melting temperature is greater than the first melting temperature.

12. The fertility-enhancing cooling seat of claim 11, wherein the paraffin comprises an inorganic paraffin.

13. A method of treatment for improving human sperm quantity and quality, comprising:
    placing the cooling seat of claim 1 on a seating surface in an environment defining an ambient temperature;
    positioning testicles adjacent the at least one of the plurality of isolated cooling cells that defines the dimension that is larger than a dimension of another of the plurality of isolated cooling cells;
    maintaining the testicles adjacent the at least one of the plurality of isolated cooling cells that defines the dimension that is larger than a dimension of another of the plurality of isolated cooling cells for a first duration, thereby causing heat of the testicles to be absorbed by the cooling seat, including the at least one of the plurality of isolated cooling cells that defines the dimension that is larger than a dimension of another of the plurality of isolated cooling cells, and causing at least a portion of the phase-change material to change from a solid to a liquid;
    causing the testicles to be removed to a position that is not adjacent to the at least one of the plurality of isolated cooling cells that defines the dimension that is larger than a dimension of another of the plurality of isolated cooling cells for a second duration, thereby exposing the cooling seat to the ambient temperature; and
    maintaining the cooling seat at the ambient temperature, thereby causing the liquid of the phase-change material to change to a solid.

14. The method of treatment of claim 13, wherein the first duration is an uninterrupted duration.

15. The method of treatment of claim 13, wherein the first duration is in a range of one to two hours.

16. The method of treatment of claim 13, wherein the first duration is in a range of two to four hours.

17. The method of treatment of claim 13, wherein the first duration is approximately the same as the second duration.

18. The method of treatment of claim 13, wherein the ambient temperature is in a range of 68° F. to 72° F.

19. A fertility-enhancing cooling seat with a plurality of isolated cooling cells for lowering temperatures of human testicles so as to increase sperm quality and quantity, comprising:
    a top flexible portion including a plurality of cooling-cell top portions and a base portion extending between the cooling-cell top portions;
    a bottom flexible portion coupled to the top flexible portion, the bottom flexible portion forming a seal with the base portion, portions of the bottom flexible portion forming a plurality of cooling-cell bottom portions, such that each cooling-cell top portion of the plurality of cooling-cell top portions in combination with a cooling-cell bottom portion defines an isolated cooling-cell volumetric space, and the plurality of cooling-cell top portions in combination with the plurality of cooling-cell bottom portions define a plurality of isolated cooling-cell volumetric spaces;
    a phase-change material located in the plurality of cooling-cell volumetric spaces, the phase-change material configured to change from a solid phase to a liquid phase at a first temperature and that is configured to change from a liquid phase to a solid phase at a second temperature that is lower than the first temperature;
    wherein the phase-change material, plurality of cooling-cell top portions and the plurality of cooling-cell bottom portions form the plurality of isolated cooling cells, and at least one of the plurality of isolated cooling cells has a volumetric space for phase-change material that is at least twice as large as the other of the plurality of isolated cooling cells;
    wherein a height of the at least one of the plurality of isolated cooling cells that has a volumetric space for phase-change material that is at least twice as large as the other of the plurality of isolated cooling cells is larger than a height of another of the plurality of isolated cooling cells and is substantially located at a position that is equidistant to a front edge and a rear edge of the cooling seat, and is closer to a right edge of the cooling seat as compared to a left edge of the cooling seat; and
    wherein the phase-change material is an alkane phase-change material and is configured to change from a solid phase to a liquid phase at the first temperature that is below 37° C. and that is configured to change from a liquid phase to a solid phase at the second temperature that is at or above 19° C.

\* \* \* \* \*